United States Patent [19]

Fiedler

[11] 4,023,678

[45] May 17, 1977

[54] PACKAGE AND IDENTIFICATION RECORD FOR AN INTRAUTERINE DEVICE

[76] Inventor: Dolores E. Fiedler, 68-15 Eliot Ave., Middle Village, N.Y. 11379

[22] Filed: Dec. 29, 1975

[21] Appl. No.: 645,019

Related U.S. Application Data

[63] Continuation-in-part of Ser. No. 484,783, July 1, 1974, abandoned.

[52] U.S. Cl. .............................. 206/363; 206/476; 206/459; 206/438; 206/485
[51] Int. Cl.² .................. B65D 83/10; A61B 19/02
[58] Field of Search .......... 206/476, 363, 459, 438, 206/DIG. 22, 534, 329, 485

[56] References Cited

UNITED STATES PATENTS

| | | | |
|---|---|---|---|
| 1,779,146 | 10/1930 | Reckford | 206/476 |
| 1,840,908 | 1/1932 | Lozier et al. | 206/232 X |
| 2,005,135 | 6/1935 | Esterson | 206/232 |
| 2,135,134 | 11/1938 | Ehlers | 206/485 X |
| 2,738,061 | 3/1956 | Roth | 206/476 |
| 3,347,358 | 10/1967 | Meyers | 206/459 X |
| 3,353,664 | 11/1967 | Armentrout et al. | 206/459 X |
| 3,358,824 | 12/1967 | Stagnitto | 206/459 |
| 3,448,737 | 6/1969 | Huck | 206/438 X |
| 3,822,783 | 7/1974 | Mortznsen | 206/329 X |

FOREIGN PATENTS OR APPLICATIONS 111,301 8/1940 Australia .................... 206/362

*Primary Examiner*—George E. Lowrance
*Assistant Examiner*—Douglas B. Farrow
*Attorney, Agent, or Firm*—Eugene E. Geoffrey, Jr.

[57] ABSTRACT

The combination of an intrauterine device and a package therefor, said package having an elongated strip of material, means on the strip for supporting the device and an identification record detachably secured to said strip.

2 Claims, 5 Drawing Figures

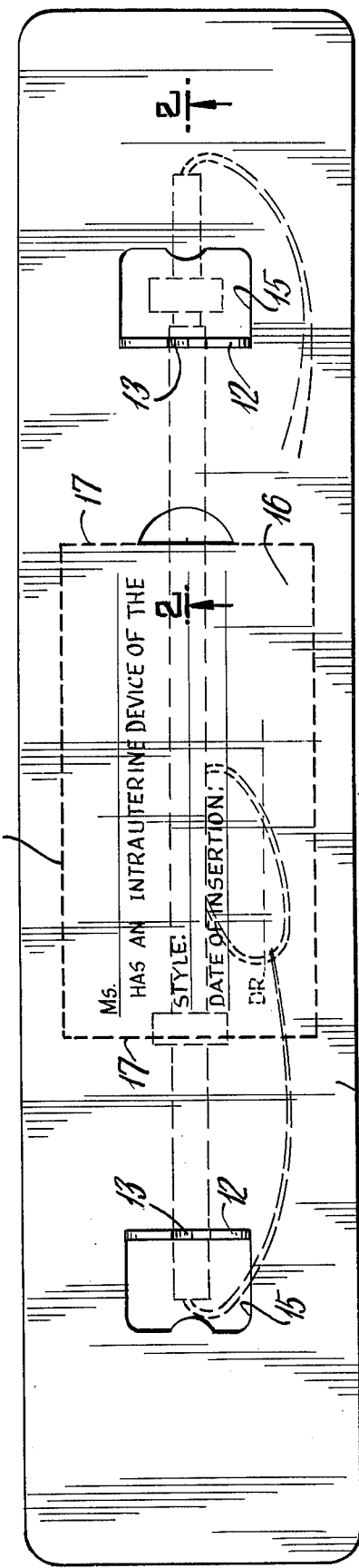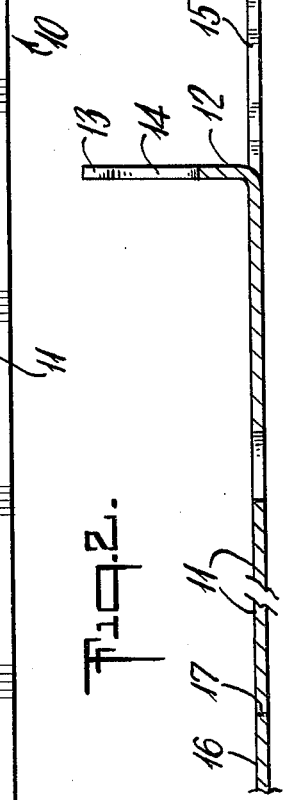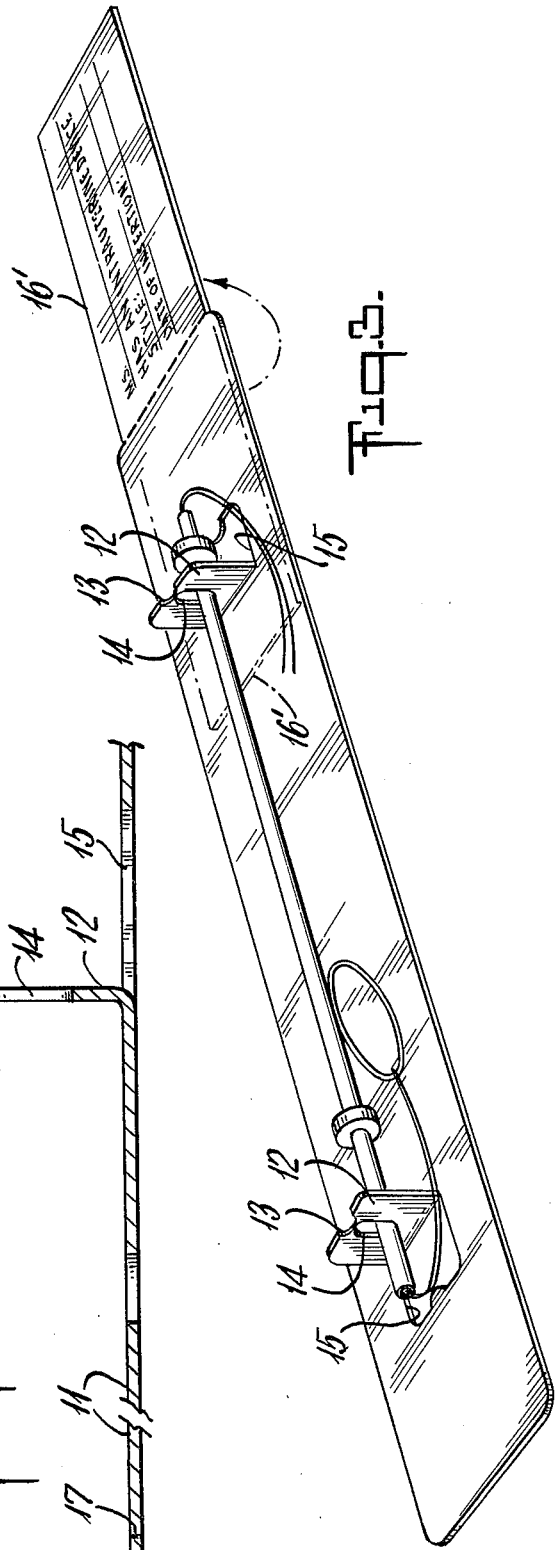

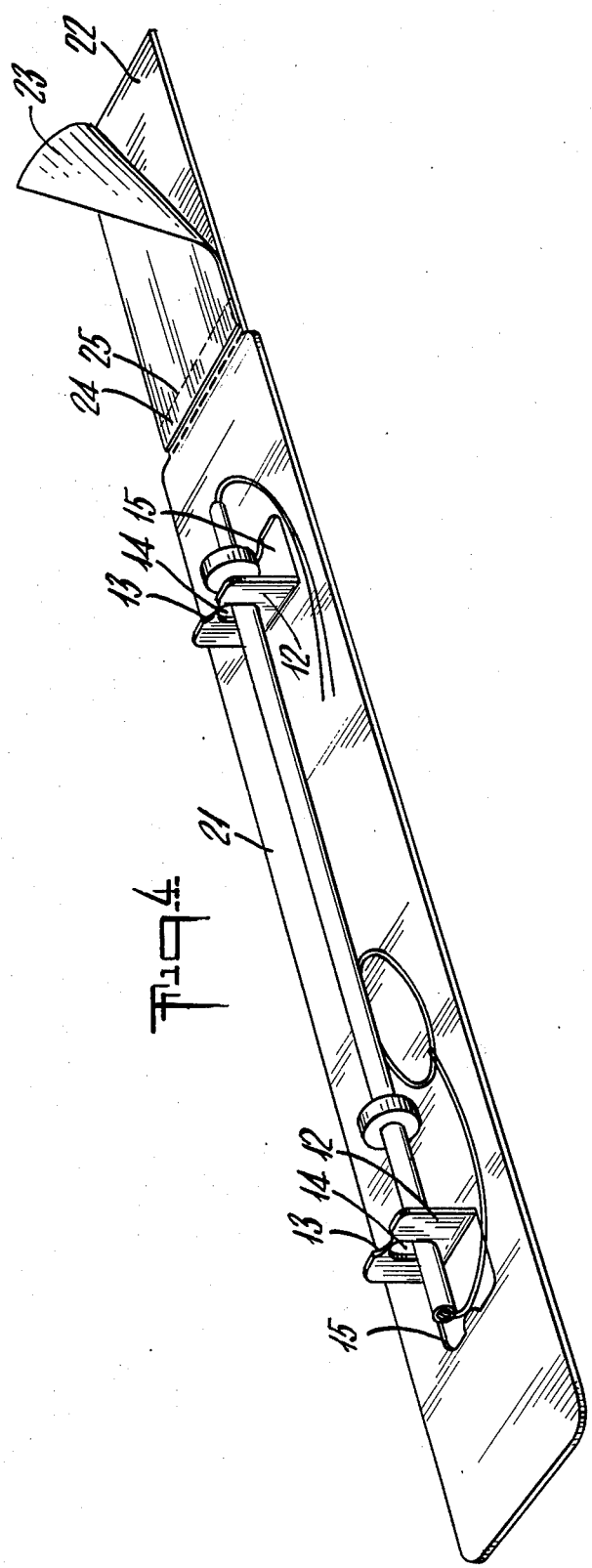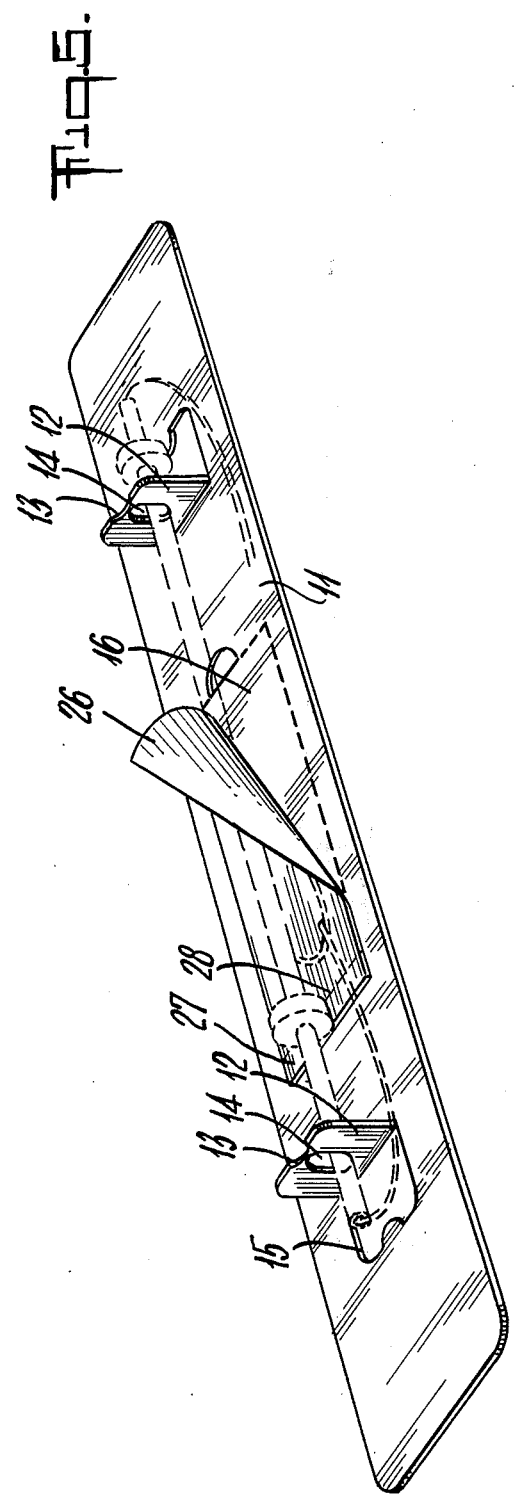

PACKAGE AND IDENTIFICATION RECORD FOR AN INTRAUTERINE DEVICE

This application is a continuation in part application of application Ser. No. 484,783, filed July 1, 1974, now abandoned, entitled Package and Identification Record for an Intrauterine Device.

This invention relates to a package for containing an intrauterine device and more specifically to a novel and improved package embodying an identification record which may readily be removed from the package. The record includes provision for the insertion of pertinent information in order to provide the user with a permanent record including the type of device and date of insertion and a duplicate of the record may be provided for the doctor.

Intrauterine devices have presented a problem for both the doctor and the user in that it is important that the device be removed periodically and the procedure for removal depends on the type of device. Very often the user does not remember either the type of device or the date of insertion with the result that they may be worn for too long a period and the doctor cannot remove it without first making an X-ray examination to determine the type. While the use of various types of informational forms have been considered, they are usually lost or mislaid and unless the same doctor is consulted, difficulty is obviously entailed.

This invention has as one of its objects the provision of a novel and improved package embodying an identification record of durable material and one on which the doctor may insert pertinent information. The record is preferably a card of wallet size that may readily be carried in a wallet and at the same time provide an authentic record that cannot be readily reproduced by the user in the event it is lost.

Another object of the invention resides in the provision of a novel and improved package for intrauterine devices having an identification record which is readily detachable from the remainder of the package for completion by the doctor.

Still another object of the invention resides in a novel and improved package for intrauterine devices.

The above and other objects and advantages of the invention will become more apparent from the following description and accompanying drawings forming part of this application.

In the drawings:

FIG. 1 is a plan view of one embodiment of the invention.

FIG. 2 is a cross sectional view of FIG. 1 taken along the line 2—2 thereof, and FIG. 3 is a perspective view of a modified embodiment of the invention.

FIGS. 4 and 5 are perspective views of modified embodiments of the invention.

Referring now to the drawings and more specifically to FIGS. 1 and 2 thereof, the package in accordance with the invention is generally denoted by the numeral 10 and comprises an elongated strip of material 11 formed of a relatively stiff material such as paper board, plastic or the like. A pair of supports 12 have notches 13 in the upper edge thereof as seen more clearly in FIG. 3 and openings 14 to receive and hold an elongated rod having the intrauterine device removably attached to one end thereof. The device is denoted by the numeral 10' and is shown in position on the supports 12.

The supports 12 may either be attached to the elongated strip 11 or they may be formed from the strip itself by cutting the strip along the lines 15 forming three sides of the support 12 and then bending the support outwardly to assume a position substantially normal to the strip.

An identification card 16 for completion by the doctor is formed by perforating the strip 12 along the lines 17 so that the card can be readily removed from the strip. It is evident, however, that other procedures may be utilized to make the card 16 easily detachable from the strip such as compressing the strip along the lines 17 or providing a series of spaced slits with extremely narrow portions remaining therebetween that may be readily broken to remove the card. With this arrangement an authentic card is provided for the user so that any doctor consulted will have sufficient information to render advice to the user and even remove the device it necessary without the need for an X-ray examination.

A modified embodiment of the invention is shown in FIG. 3 wherein components corresponding to those of FIGS. 1 and 2 are denoted by like numerals. In this figure the identification card 16' is detachably connected to the strip of material 11 along the line 18. The card 16' is normally folded underneath the strip as shown in phantom and is merely unfolded and detached by the doctor.

A modified embodiment of the invention is shown in FIG. 4. In this embodiment the elongated strip is denoted by the numeral 21 and corresponds to the strip 11 of FIG. 3. The supports for the intrauterine device are identical to those shown in FIG. 3 and like numerals are used to denote like components thereof. One end of the strip 21 includes a detachable card 22 and an overlying sheet of paper or other similar material 23 cemented at one end 24 to the card 22. The sheet 23 is perforated along the line 25 and carries on the underside thereof a coating such as carbon or the equivalent. Both the card 22 and the overlying sheet 23 are preferably imprinted in the manner of the cards shown in FIGS. 1 and 3 to facilitate insertion of information such as the type of device, date of insertion, name of doctor and the like. The doctor can then remove sheet 23 for his records and give the duplicate card to the user.

The form of the invention shown in FIG. 5 is similar to that shown in FIG. 1 and like numerals have been used to denote like components. A sheet 26 imprinted in the same manner as the card 16 is attached thereto at one end 27 and perforated along the line 28. The sheet 26 has a coating of carbon or other similar reproducing material so that the doctor upon completing the form on the sheet 26 provides a duplicate record on the card 16. Thus both the doctor and the user will have permanent records.

In each embodiment of the invention it is understood that the intrauterine device together with the elongated insertion rod carried by the structure 10 is in turn housed in a suitable carton or enclosed in a plastic wrapping.

While only certain embodiments of the invention have been illustrated and described, it is understood that alteration, changes and modifications may be made without departing from the true scope and spirit of the invention.

What is claimed is:

1. The combination of a package and an intrauterine device comprising an elongated strip of material having a length at least equal to the length of said device including the support therefor, and a pair of longitudinally spaced supports extending from one surface of said strip engaging and retaining said device in position thereon, said strip of material including an area within the confines of said strip defined by a line of perforations in said material forming a card having indicia for the insertion of pertinent data thereon to provide a permanent record for the user of said device.

2. A continuation according to claim 1 wherein said strip further includes a sheet overlying said card and affixed to said strip along at least one edge of said card to provide a duplicate record.

* * * * *